United States Patent [19]

Ogunro

[11] Patent Number: 4,559,055
[45] Date of Patent: Dec. 17, 1985

[54] SELECTIVELY REMOVABLE PROSTHETIC NAIL

[76] Inventor: E. Olayinka Ogunro, 625 Ray Ave., DeSoto, Tex. 75115

[21] Appl. No.: 599,981

[22] Filed: Apr. 13, 1984

[51] Int. Cl.$^4$ ................................................ A61F 1/00
[52] U.S. Cl. ........................................ 623/11; 132/73
[58] Field of Search ..................... 3/1, 1 C; 128/81 R, 128/81 A, 77, 92 C; 132/73, 88.5, 88.7

[56] References Cited

U.S. PATENT DOCUMENTS 4,445,234  5/1984  Ogunro ........................................ 3/1

FOREIGN PATENT DOCUMENTS 661624  11/1951  United Kingdom ................... 132/73

OTHER PUBLICATIONS

"A Study of Nail Bed Injuries: Causes, Treatment, and Prognosis" by Zook, Guy and Russell; *The Journal of Hand Surgery*, Mar. 1984.

Primary Examiner—Richard J. Apley
Assistant Examiner—James Prizant
Attorney, Agent, or Firm—Charles W. McHugh

[57] ABSTRACT

A selectively removable prosthetic nail adapted for use on one of the digits of a person's hand or foot, including a nail plate comprising a sheet having front and rear ends and a longitudinal axis extending therebetween. A bifurcated anchor member extends downwardly from near the front end of the nail plate; the member has two legs with proximal and distal portions. The distal portions of the legs have a rest condition at which they are spaced apart appreciably further than are their proximal portions, and the distal portions are susceptible of being temporarily brought together so that their distal portions are essentially as close as are their proximal portions. The two legs preferably lie in a transverse plane where they are exposed to being externally gripped (by tweezers or the like) from the front of the nail plate. The nail plate is held in place on a digit when the distal portions of the legs are in their rest condition and when they are in contact with a pocket of tissue on the forward end of a person's digit. When the distal portions of the legs are temporarily brought together, the anchor member may be lifted vertically away from the person's nail bed without damaging the pocket of tissue. When desired, the prosthetic nail may be replaced on the digit without any new surgery, and may even be replaced at home by the wearer.

6 Claims, 4 Drawing Figures

U.S. Patent  Dec. 17, 1985  4,559,055
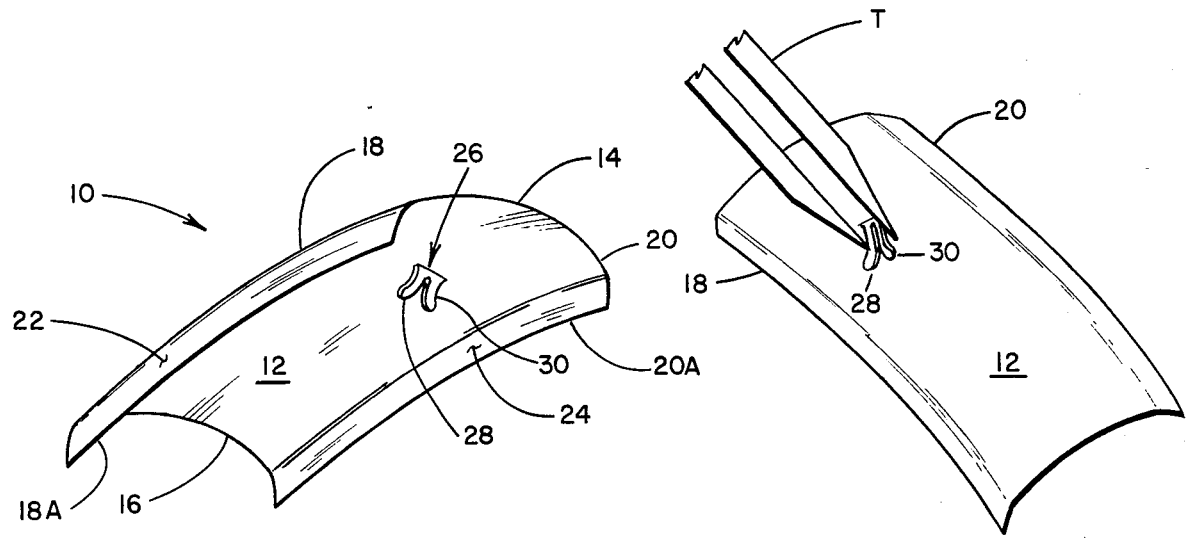
FIG. 1   FIG. 2
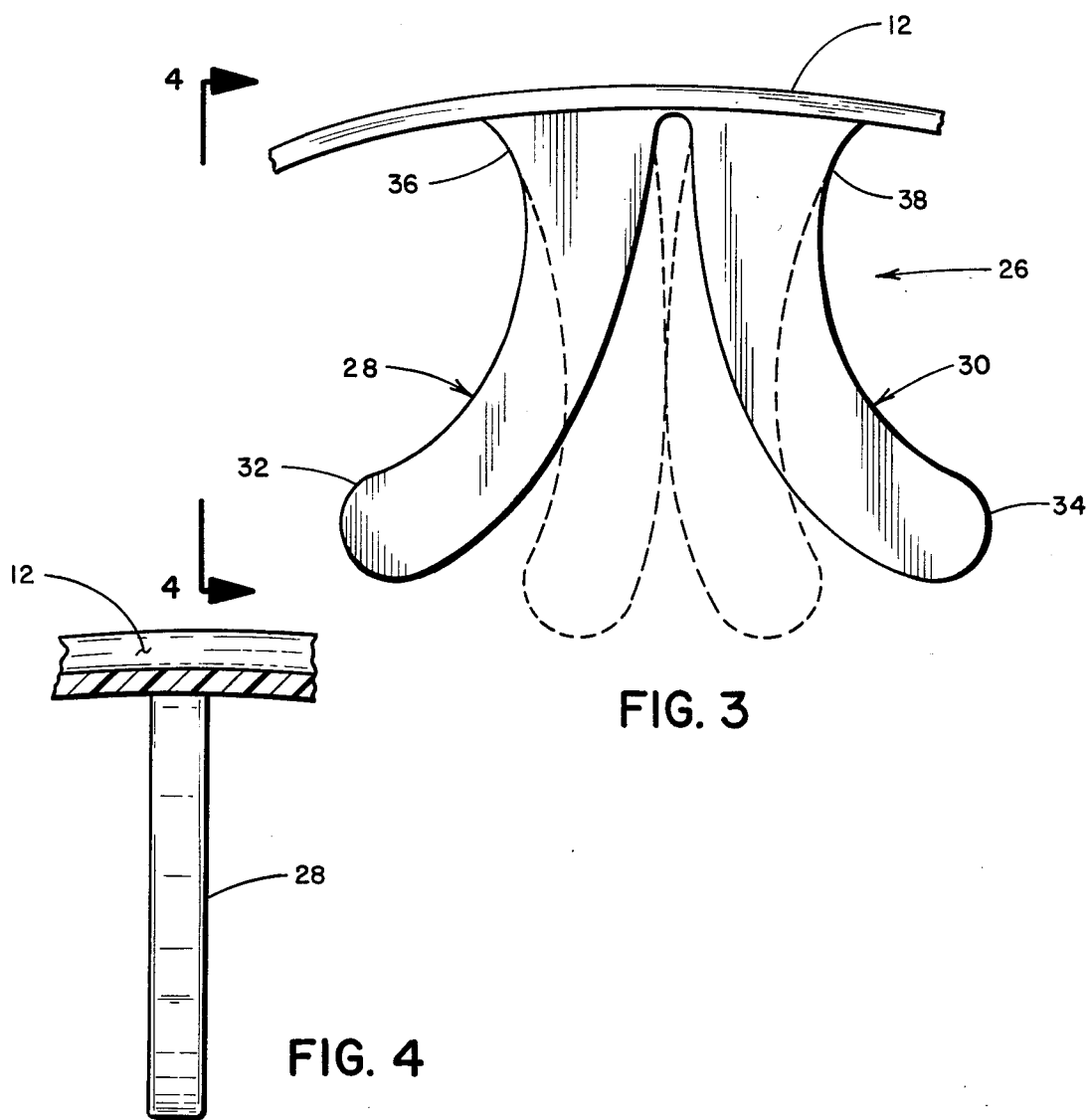
FIG. 3
FIG. 4

SELECTIVELY REMOVABLE PROSTHETIC NAIL

CROSS-REFERENCE TO RELATED APPLICATION

This application discloses subject matter that is similar to earlier-filed and co-pending U.S. application Ser. No. 399,477 filed July 19, 1982 entitled "Prosthetic Nail," now U.S. Pat. No. 4,445,234.

BACKGROUND OF THE INVENTION

This invention relates generally to prosthetic nails for humans; more particularly, it relates to a prosthetic nail which is adapted to be surgically fitted to a finger or a toe so as to entirely replace a damaged or diseased nail.

It is well known that there are several million injuries to the fingertips that occur every year. This should not be surprising when one stops to think about how much humans depend on their hands in daily living, and how the hands are exposed to so many dangerous environments—including proximity to knives, hammers, drills, needles, farm implements, mallets, chisels, punches, grinders, air wrenches, shears, presses, clamps, saws, cutters, torches and other tools and machinery. In fact, it has been stated that about 30 to 40 percent of the annual industrial compensation payments to workers in the United States result from all types of injuries to the hand; and injuries to the fingertips constitute a large portion of those injuries.

In addition to debilitating injuries to the fingertips that are caused by accidents, there are also infections that can afflict the fingers in such a way as to render the nail functionally useless and/or so distorted as to even constitute an embarassment There are fungi, for example, that can eventually convert a fingernail from a smooth, thin plate into a thick, irregular mass of hardened tissue bearing more resemblance to a 10 massive scab than to a fingernail.

In addition to a person's fingers, the digits of a foot (i.e., the toes) are also vulnerable to many kinds of injuries. Lawn mowers in particular seem to contribute to many cutting injuries; the dropping of heavy objects on the leading edge of a foot naturally contributes to many crushing injuries to the toes.

There has existed, therefore, a need for a prosthetic nail which can be used to replace in its entirety a natural nail that has become severaily injured or diseased. This is not to say that there has never been any attempt to create an artificial nail for humans. In fact, there have been two reports in the journal "Plastic and Reconstructive Surgery" of previous efforts to create a fingernail of acrylic resin material that is glued to the nail bed of the finger. One of these reports describe work done by H. J. Buncke, Jr. and R. J. Gonzalez; the report is entitled "Fingernail Reconstruction" and it appears at Volume 30, pages 452–461 of "Plastic and Reconstructive Surgery" (1962). Another article entitled "Replacement of a Malformed Fingernail with Acrylic Resin Material" describes work by B. N. Bautista and S. B. Nery; it appears in the same journal at Volume 55, pages 234–236 (1975). Reference to other problems with fingers can be found in Chapter 32 of the book entitled *Plastic Surgery,* 3rd Edition, edited by William C. Grubbs and James W. Smith, published by Little, Brown and Co. (1979). And, of course, there exits another form of what some might call "prior art," namely, the cosmetic nails that are sold in many stores for self-application (using an adhesive); these relatively cheap plastic nails are sold for the purpose of mending a broken nail or adding an apparent length to a short nail. Such cosmetic nails are merely glued on top of an existing fingernail or toenail in order to create what is described as a more pleasing appearance. Of course, such plastic appendages depend upon a natural nail for their connection to the finger or toe, and they have no structural features which would render then independently operable as prosthetic nails.

To meet the need for a prosthetic nail that is both medically acceptable and cosmetically pleasing, the earlier-referenced disclosure in U.S. Pat. No. 4,445,234 has been proposed as one way of solving the problems described above. However, the invention disclosed in that patent is essentially restricted to installation and/or removal by a surgeon, and both the installation and replacement of a prosthetic nail (when required) would involve what most laymen would call—at least—a "minor operation." That is, if a prosthetic nail should be damaged or cracked, or if an infection should somehow develop under the prosthetic nail, a surgeon would almost surely have to remove the prosthetic nail of that earlier design.

The cleanliness of a person's nail bed underneath the prosthetic nail could be more readily assured if there was some way to periodically remove a prosthetic nail, so that the bed could be cleansed with alcohol or the like, and then the nail could be replaced without the necessity of visiting a surgeon's office. It has now been determined that this is entirely feasible—by virtue of using a structure like that disclosed herein. Accordingly, it is an objection of this disclosure to reveal a structure that is capable of being selectively installed and removed from one of the digits of a person's hand or foot—without the necessity for repeated surgical procedures.

It is another object of this invention to foster a more relaxed attitude on the part of the wearer of a prosthetic nail, because the wearer need not be quite so protective of the nail—knowing that it can be easily replaced if it should become damaged as a result of strenuous activity.

Still another object is to provide a prosthetic nail which is selectively replaceable when either desired or required by the wearer, to satisfy either cosmetic preferences or structural needs, all without the necessity for repeated surgical involvement.

These and other objects will be apparent from a study of the specification and the claims attached hereto, as well as reference to the accompanying drawing.

BRIEF DESCRIPTION OF THE FIGURES

FIG. 1 is a perspective view of one embodiment of the invention which has depending sides or "skirts";

FIG. 2 is a perspective view of another embodiment of the prosthetic nail—and having no side "skirts";

FIG. 3 is a front elevational view of the nail as shown in FIG. 1, with its rest position shown in solid lines; and FIG. 4 is a fragmentary side view of a nail and its depending legs, partially cross-sectioned, taken in the plane indicated by lines 4—4 in FIG. 3.

DETAILED DESCRIPTION OF THE PREFERRED EMBODIMENT OF THE INVENTION

Referring initially to FIG. 1, a prosthetic nail 10 in accordance with this invention includes a nail plate 12 consisting of a sheet of material which is compatible with the human body and having a front end 14 and a rear end 16. A preferred material for the sheet is a thin (e.g., about 0.015 to 0.020 in.) piece of polypropylene; more specifically, an unmodified homopolymar of the type sold by Hercules Incorporated of Willmington, Del. under the trademark "Profax 6523" is believed to be particularly appropriate. A thin sheet of this polypropylene will have an essentially translucent character so that the blood vessels near the end of a person's digit will be sufficiently perceptible as to provide an essentially variegated pinkish color—almost matching a person's natural fingernails. The tensile strength of such a material (typically 4300-5500 PSI) will be quite adequate for handling the loads to which the prosthetic nail 10 will likely be subjected.

The plate 12 is sized so that it may be placed on top of the distal end of a digit in such a way that the longitudinal axis of the plate extends in the same general direction as the distal phalangeal bone of the digit. In the preferred embodiment, the length of the plate 12 is about 2.4 cm as manufactured, and the width is about 1.5 cm. But, the material from which the preferred plate is manufactured is sufficiently soft as to be readily susceptible to being cut with ordinary scissors, so that the plate may be configured for matching the size of other, natural nails—in order that the artificial nail will not be so noticeable. As viewed in a transverse cross-section, then, the plate 12 is slightly curved so as to approach the generally cylindrical cross-sectional shape of a typical digit. The right edge 18 and the left edge 20 of the plate 12 may be formed by terminating the plate's width in the general plane of the plate; in such a case, it would be easy for anyone with scissors to cut small portions off the sides of the plate in order to make it fit the associated digit. An advantage of such an embodiment is that the plate 12 can be supplied in a relatively wide condition—and trimmed by one or more millimeters along each side as appropriate to meet a particular medical requirement. In a preferred embodiment, the right and left edges lie in a plane that is spaced a slight distance away from the plane of the plate. These edges 18A, 20A would then be connected to the main body of the plate 12 by short, elongated portions or skirts. These skirts 22, 24 can be medically beneficial in that they provide a downwardly extending structure which can bear against the sides of the nail bed and help preclude the entrance of dirt or other contaminants through the sides of the prosthetic nail. These depending skirts 22, 24 are also useful in providing lateral stability for a prosthetic nail, so that the nail has less tendency to shift with respect to a digit when the nail is subjected to transverse loading. Of course, in a nail embodiment having depending skirts such as skirts 22, 24, there is no way to adjust the nail size to make it more narrow after it has been fabricated; hence, a much greater inventory of nail sizes must be maintained by a surgeon so that he will have at his disposal a nail that is reasonably assured of constituting an acceptable "fit" on a particular patient.

Extending downwardly from near the front end of the nail plate 12 is a bifurcated anchor member 26. Said anchor member has two legs 28, 30, each of which has proximal and distal portions. The leg distal portions 32, 34 have a rest condition at which they are spaced apart appreciably further than are their proximal portions. Also, the distal portions 32, 34 are susceptible of being temporarily forced together, so that the distal portions can be made to be essentially as close as their proximal portions 36, 38. The two legs 28, 30 lie in a generally transverse plane where they are exposed to being externally gripped from the front of the nail plate—by tweezers or the like.

Turning next to FIG. 2, an illustration of one embodiment of the prosthetic nail—having no depending skirts along the sides—is shown with exemplary tweezers T; the tweezers are shown in a configuration as if they were being manually squeezed, such that they are applying a compressive force against the outside surfaces of the legs 28, 30. When this compressive force has been applied to the legs, the resilience of the plastic material from which the legs are formed causes the distal ends 32, 34 to be brought toward one another. And, when sufficient force has been applied, the distance between the outer surfaces of the distal portions 32, 34 can be essentially the same as the distance between outer surfaces of the proximal portions 36, 38. Under these conditions, it would be feasible to lift the anchor member 26 vertically away from a person's nail bed without unduly distorting or damaging a pocket of tissue in said nail bed.

Referring additionally to FIG. 3, the two legs 28, 30 are shown with solid lines in their rest condition, and shown with broken lines in their (temporary) compressed condition. This figure probably best illustrates the two conditions or modes wherein the inherent resilience of the leg material is used to provide the desired engagement between a prosthetic nail 10 and the person's nail bed. While relying on leg resilience to cause the distal end of a leg to rest below some tissue in order to achieve selective engagement, it is true that another way of achieving such an engagement would be to have hinged legs which possess minimal, if any, inherent resilience. Where a hinge is relied upon as the technique for moving a leg to and from its "rest" or latching condition, there is the necessity of providing some structural member (like a wedge) which will preclude rotation of a rigid leg about its associated hinge axis. The possibility of losing or breaking such a structural member would always exist, though, so the embodiment having an appropriate degree of inherent resilience in at least one of two legs is definitely the preferred embodiment.

Dimensionally, the bifurcated anchor member 26 includes legs that extend downwardly from the plate for about 4 mm; that is, the most remote part of a leg is preferably less than 5 mm from the bottom of the plate 12. By limiting the length of the depending legs 28, 30 to 5 mm or less, there will be less chance of physical contact between any bone structure and a depending leg. Any accidental blow to the top of the plate 12 will therefore tend to be cushioned by soft tissue on the digit, thereby making the prosthetic nail less sensitive to normal manual activity involving contact with a digit's surroundings.

The side-to-side spread of the distal ends 32, 34 is preferably about 6 mm when the legs 28, 30 are in their rest mode; when temporarily forced together, the distal portions are preferably about 3 mm apart (from outside surface to outside surface). Hence, the outside surface of the distal portions 32, 34 are spaced appreciably further than are their proximal portions—when the legs 28, 30 are at rest. The increased 3 mm of distal width when the legs 28, 30 are relaxed is sufficient to provide significant resistance against upward movement of a plate 12 away from the tissue in a digit. While 3 mm may not seem like much in an absolute sense, it is believed to be enough to hold a prosthetic nail 10 on a digit even when that nail is being used in a functional way, e.g., to scratch some skin that is itching, etc. At a minimum, the tissue on a person's digit will grow around the two depending legs 28, 30 by an amount to permit pinching action between two fingernails, so that a needle or the like could be grasped and lifted. In order that there will be enough structural integrity in the legs 28, 30, it is preferred that they have a cross-sectional area of at least 0.5 sq. mm; and, this is preferably accomplished by making the width of a leg about 1 mm and its depth (from front to rear) about 0.5 mm. Furthermore, to simplify insertion of a leg into a prepared socket, it is preferred that the distal end of a leg have ample radii—even to the point of being essentially round. The reason for preferring a cross-sectional area which is wider than it is deep (or thick) is to insure that the legs will have a larger area moment of inertia about the axis about which the leg flexes when it is squeezed with tweezers or the like. That is, it is easier to bend the legs 28, 30 in a direction that is parallel to the longitudinal axis of the plate 12 than it is to bend the legs transversely. However, the reason for wanting greater rigidity in the legs (by virtue of their geometry) is not because of any desire to require more work during the installation process for a prosthetic nail. Instead, extra resistance against flexing of a leg during installation is preferred because of the recognition that the same amount of flexing—and work—would be required to remove a prosthetic nail. Therefore, during routine use of a person's hand in carrying out ordinary tasks, the forces which may be deliberately or accidentally imposed on the prosthetic nail and which would tend to pull it away from its associated nail bed will be more readily resisted when a leg is oriented so that it is predominantly transverse in orientation rather than longitudinal.

Referring still to FIG. 3, it will be noted that there is a significant space between the two depending legs 28, 30 near the proximal ends of the legs—when the legs are in their rest condition. This space is provided so that there will be sufficient clearance in order to accomodate material of the two legs as they are forced together. The broken line showing of the two legs, wherein they are squeezed together, should make it readily apparent as to why an ample clearance space is provided between two relatively solid legs. However, to the extent that the material from which the legs are formed is more soft and capable of being at least slightly distorted, the "clearance" space between the legs could be reduced.

During fabrication of a prosthetic nail in accordance with this invention, the anchor member 26 will typically be cast or otherwise prepared as a distinct element—and then combined with a generally planar plate 12 by ultrasonic welding or a particularly effective glue, etc. But the nail may also be cast as an integral unit, using a flexible mold or a rigid mold with movable cores. 15 Once the anchor member has been secured to a plate 12, the prosthetic nail 10 will typically be sterilized and packaged with a pair of tweezers T or any other appropriate installation tool. A surgeon will then open the sterilized package at a later time and insert the prosthetic nail into a space that has been surgically prepared to receive the nail. By temporarily forcing the two legs together, the distal end of those legs may be caused to engage (and eventually lie under) a small amount of tissue. At any desired time, the prosthetic nail 10 can be removed from the digit by reversing the installation procedure, i.e., forcing the legs together and then lifting the plate away from the nail bed. If such a removed nail 10 is still structurally sound, it can be cleaned with alcohol or some other antiseptic solution and, when desired, returned to its use position. Alternatively, if the nail is deemed to be cracked, discolored or otherwise unserviceable, the patient can simply tear open a new package and install a brand new nail—reversing the way he removed a previous prosthetic nail, all without the need for any additional surgical monitoring.

While only the preferred embodiments of the invention have been disclosed herein in great detail, it will be apparent to those skilled in the art that modifications thereof can be made without departing from the spirit of the invention. Thus, the specific structure shown herein is intended to be exemplary and is not meant to be limiting, except as described in the claims appended hereto.

What is claimed is:

1. A prosthetic nail adapted for use on one of the digits of a person's hand or foot, comprising the combination of:

(a) a nail plate comprising a sheet having front and rear ends and a longitudinal axis extending therebetween, and the plate being adapted to be placed on top of the distal end of a digit so that the longitudinal axis extends in the same general direction as to the distal phalangeal bone of the digit, and said plate being slightly curved as viewed in a transverse plane so as to approach the generally cylindrical cross-sectional shape of a typical digit, and said plate having a thin edge at its rear end that is adapted to be at least partially buried within the eponychial fold of the digit; and (b) a bifurcated anchor member extending downwardly from near the front end of the nail plate, and said anchor member having two legs with proximal and distal portions, and the distal portions of the legs having a rest condition at which they are spaced apart appreciably further than are their proximal portions, and said distal portions being susceptible of being temporarily brought together so that the distal portions are essentially as close as are the proximal portions, and the two legs lying in a transverse plane where they are exposed to being externally gripped from the front of the nail plate, whereby the nail plate is held in place on a digit when the leg distal portions are in their rest condition and when they are in contact with a pocket of tissue on the forward end of a person's digit, and whereby said leg distal portions may be temporarily brought together so that the anchor member may be lifted vertically away from the person's nail bed without damaging the pocket of tissue.

2. The prosthetic nail as claimed in claim 1 wherein the bifurcated anchor member is located very close to the front end of the nail plate, and wherein a significant gap is provided between the two legs of the anchor member, and the outside surfaces of said legs being configured so as to be engageable by the two jaws of a pair of tweezers, whereby the anchor member may be released from its holding mode to its release mode by squeezing tweezers around the two legs of the anchor member in a transverse direction.

3. The prosthetic nail as claimed in claim 1 wherein the anchor member is molded from a plastic material having an inherent resilience and a sufficient memory as to cause the legs to return to their extended positions within a relatively short period of time after a compressing force has been removed from the outer surfaces of said legs.

4. The prosthetic nail as claimed in claim 1 wherein the distal ends of the two legs are separated by a distance that is at least twice the narrowest distance between the proximal ends of the legs.

5. The prosthetic nail as claimed in claim 1 wherein the distal ends of the two legs are separated by a distance which is approximately 3 mm greater than the distance separating the proximal portions of said legs, whereby there is a potential of holding the prosthetic nail on a person's digit by having tissue overlie the distal portions of the two legs by as much as approximately 3 mm.

6. The prosthetic nail as claimed in claim 1 wherein each of the legs extends downwardly from its attachment point for a distance of about 4½ mm.

* * * * *